United States Patent [19]

Berke et al.

[11] Patent Number: 4,711,230

[45] Date of Patent: Dec. 8, 1987

[54] CHIROPRACTIC ADJUSTMENT DEVICE

[76] Inventors: Michael Berke; Matthew Rosman, both of 2070 Hidden Glen Dr., Marietta, Ga. 30067

[21] Appl. No.: 869,734

[22] Filed: Jun. 2, 1986

[51] Int. Cl.[4] .......... A61F 5/00

[52] U.S. Cl. .......... 128/69; 5/439; 128/75

[58] Field of Search .......... 128/69, 70, 71, 73, 128/76 R; 5/439, 440

[56] References Cited

U.S. PATENT DOCUMENTS

| | | | |
|---|---|---|---|
| 332,126 | 4/1861 | Elder | 5/439 X |
| 1,664,537 | 4/1928 | Blankinship | 5/439 |
| 2,239,003 | 4/1941 | Jones | 128/69 X |
| 2,684,064 | 7/1954 | Thompson | 128/69 |
| 2,727,510 | 12/1955 | Thompson | 128/69 |
| 2,756,744 | 7/1956 | Thompson | 128/69 |
| 2,791,215 | 5/1957 | Thompson | 128/69 |
| 2,817,857 | 12/1957 | Hockensmith | 5/440 |
| 2,987,113 | 6/1961 | Pitteroff | 5/439 |

*Primary Examiner*—Edgar S. Burr
*Assistant Examiner*—Moshe I. Cohen
*Attorney, Agent, or Firm*—Thomas & Kennedy

[57] ABSTRACT

A chiropractic adjustment device for use in applying toggle recoil to a vertebrae comprises a headrest placed upon a set of compression springs mounted atop a base. The device includes a pair of latches that have a catch formed with a series of catch elements and a latch bar for catching and holding the headrest in various positions relative to the base.

8 Claims, 4 Drawing Figures

CHIROPRACTIC ADJUSTMENT DEVICE

TECHNICAL FIELD

This invention relates to devices for use in performing chiropractic treatments.

BACKGROUND OF THE INVENTION

The Toggle-Recoil chiropractic procedure for cervical adjustment involves applying manual force abruptly to a cervical vertebrae, most commonly to the first vertebrae, which is known as the atlas, in a manner such that the head of a patient is snapped to one side and then allowed to recoil. Heretofore, this procedure has often been performed with the aid of devices developed by Joseph Clay Thompson such as those shown in U.S. Pat. Nos. 2,684,064, 2,727,510, 2,791,215, 2,886,029 and 3,343,531. Another prior art device designed for this use in cervical adjustment is that of Dr. Orville L. Puckett which is shown in U.S. Pat. No. 3,111,944.

Basically, the just mentioned devices have included a headrest that may be forced downwardly against a spring counterforce until a stop is encountered. Once the stop is struck a limited degree of recoil is inherently developed by the internal resilience of the body itself. Since the degree of such recoil is dependent upon the degree of body resiliency of the particular patient in whom it occurs, chiropractors must prejudge such body resiliency to determine the amount of force to be applied manually in order to produce the desired magnitude of recoil force. This, however, has proven to be difficult to do in a reliable and predictable manner. A hazard and limitation has also existed with regard to their use with patients of relatively rigid cervical structure who cannot tolerate substantial applications of force without risk of injury. Accordingly, the present invention is directed at providing a chiropractic adjustment device for use in practicing the Toggle-Recoil procedure which overcomes limitation and problems associated with those of the prior art.

SUMMARY OF THE INVENTION

In one form of the invention a chiropractic adjustment device comprises a base, a headrest movably supported upon the base, and spring means for biasing the headrest away from the base. The device also has latch means that includes a catch which has a series of spaced catch elements for releasably catching and holding the headrest in a plurality of spring biased positions relative to the base upon the application of forces of diverse magnitudes to the head of a patient supported upon the headrest.

In another form of the invention a chiropractic adjustment device comprises a base, a headrest mounted to the base for movement along a defined path of travel with respect thereto, and a plurality of compression springs mounted between the base and the headrest so as to bias the headrest away from the base. Latch means are provided for releasably catching and holding the headrest in a plurality of positions relative to the base upon the application of diverse forces to the headrest.

In yet another form of the invention a chiropractic adjustment device comprises a base, a pair of catches pivotably mounted to opposite sides of the base, and a set of springs mounted atop the base. A headrest is mounted atop the set of springs. A pair of latch bars is mounted to opposite sides of the headrest in engagement with the pair of catches. Each of the catches includes an elongated bar spring biased against one of the catch bars that has a linear series of teeth adapted to catch and hold the latch bars and the headrest at a plurality of positions relative to the base upon the application of forces of diverse magnitudes to the head of a patient supported upon the headrest.

DETAILED DESCRIPTION

Figure 1:
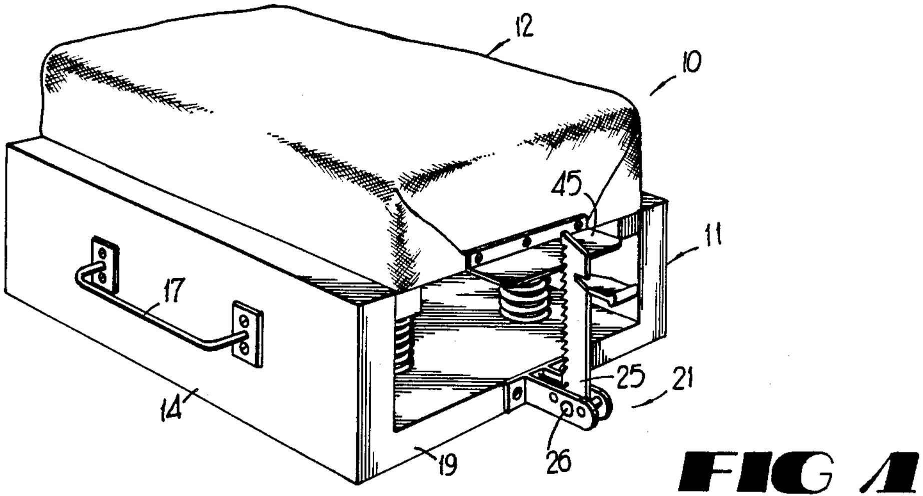
FIG. 1 is perspective view of a chiropractic adjustment device that embodies principles of the present invention in one preferred form and which is positioned in preparation for use.
Figure 2:
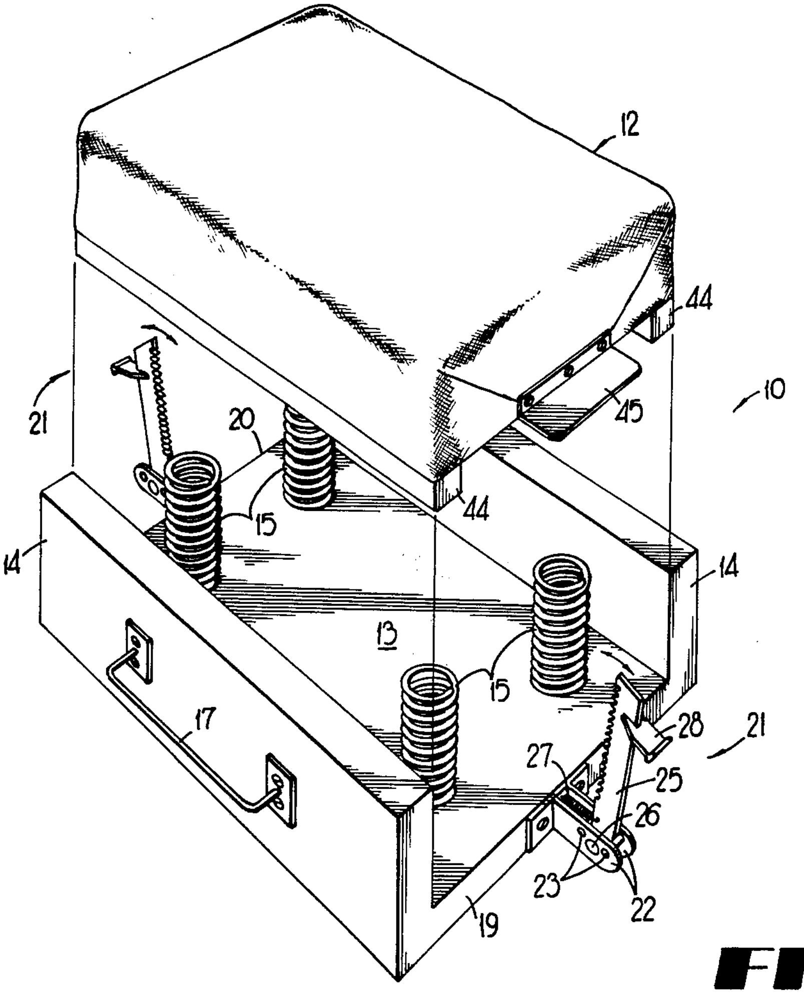
FIG. 2 is an exploded view of the chiropractic adjustment device illustrated in FIG. 1.

With reference now in detail to the drawing, there is shown a chiropractic adjustment device 10 which has a base indicated generally at 11 and a headrest indicated generally at 12. The base is of a U-shaped or channel configuration having a floor 13 from opposite sides of which upwardly extend two parallel walls 14 that here serve as a guide or track for the headrest to slide. A set of four compression springs 15 is mounted atop the floor 13 between the two side walls 14. A handle 17 is mounted to one of the base walls 14 by which the device may be manually carried.

To opposite sides 19 and 20 of the floor 13, is mounted a pair of catches of the same structure that are indicated generally at 21. Each catch is seen to include a pair of spaced arms 22 which project laterally from the floor in parallel relation. Each pair of arms are spanned and held apart by a pair of pins 23 that also function as stops. Between each pair of pins 23 is mounted a pivot pin 26 to which is pivoted an elongated catch bar 25. A tension spring 27 biases the catch bar 25 rotatably towards the top of the floor 13 of the base. A pull tab 28 is rigidly mounted to each catch bar near its top for manually rotating the bar about pivot pin 26 away from the top of the base floor momentarily to release it from a latch bar.

Figure 4:
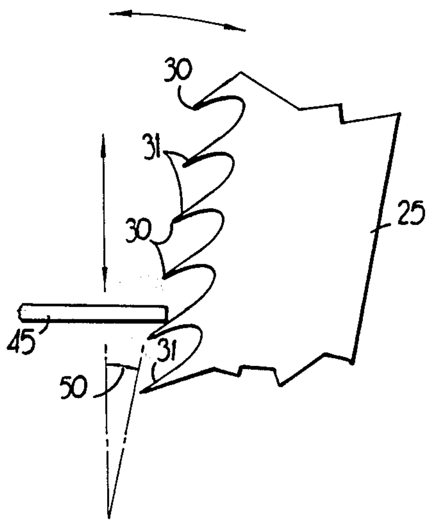
FIG. 4 is a fragmentary, side elevational view of a portion of one of the two latches of the device illustrated in FIG. 1.

As shown most clearly in FIG. 4, the upright edge of each catch bar 25 located proximally to the base is provided with a series of teeth or catch elements whose tips 30 are located equidistantly apart along a linear edge of the catch bar 25. The teeth are seen to pitch downwardly somewhat with their upper surfaces 31 sloping downwardly towards the plane in which pivot pin 26 is located.

Figure 3:
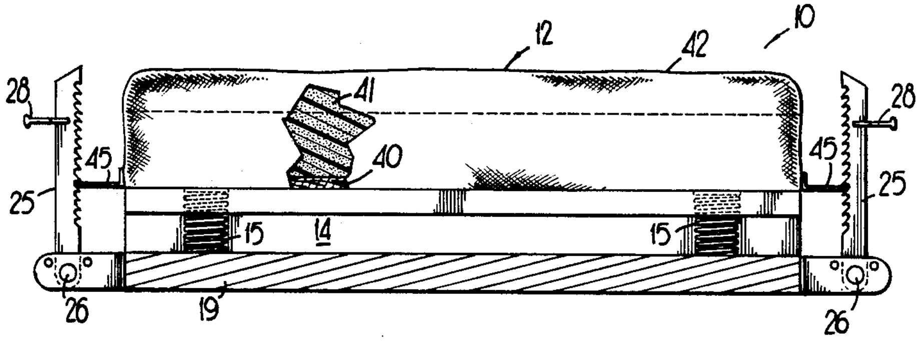
FIG. 3 is a side elevational view, in cross-section, of the chiropractic adjustment device shown in FIG. 1 which is in a position immediately following use.

The headrest 12, shown in most detail in FIG. 3, is constructed of a block 40 atop which is mounted a foam rubber cushion 41. The block and cushion are jointly covered with fabric 42. A pair of slide rails 44 is mounted to opposite sides of the bottom of the block 40. A pair of latch bars 45 is mounted to other, opposite sides of the block so as to project laterally from the headrest. The latch bars 45 and the catch bars 25 collectively provide two latches for releasably latching the headrest to the base in several positions of the headrest with respect to the base.

In preparing the adjustment device for clinical use the base 11 is set atop a table or the like and headrest 12 set loosely atop the four compression springs 15 with the slide rails 44 positioned just within the bounds of the upright walls 14 of the base. The two latch bars 45 are positioned between two of the catch elements or teeth 30 adjacent the upper end of the catch bar 25, as shown in FIG. 1. A chiropractor may now position the head of a patient upon the headrest with either the patient's right or left cheek set in intimate contact therewith. The chiropractor then applies manual force abruptly and downwardly to the vertebrae to be treated. This abrupt downward force causes the patient's head and the headrest to move abruptly downwardly against the counterbias provided by the compression springs 25.

As best understood by reference to FIG. 4, as the headrest moves down, the latch bars 45 move atop the sloping upper surfaces 31 of the teeth or catch elements in succession. This causes the catch bar 25 to be cammed so as to pivot clockwise, as viewed in FIG. 4, against the counterforce provided by the tension spring 27 so that the latch bar 45 moves from one tooth to the next. Downward movement of the headrest towards the floor of the base continues until its movement has been arrested by the force of the compression springs. After this occurs the compression springs force the headrest to move back upwardly. The latch bars 45 accompany this upwardly movement of the headrest to which they are rigidly secured. As may be appreciated from FIG. 4, this permits the catch bar 25 to pivot counterclockwise under the force of the tension spring 27 and thereby decrease angle 50 and bring a tip 30 of the tooth immediately above the latch bar 45 into a position to intercept the vertical path of bar travel indicated by the double headed arrow. This upward travel between the position of the latch bar shown in FIG. 4 until it engages and is caught by the tooth above it thereby producing a recoil force. Thus, with the present adjustment device the headrest is not merely urged downwardly to an abrupt stop but rather is urged downwardly a distance in proportion to the clinical force applied and then permitted to move back upwardly a short distance to provide positive recoil. In addition, since a stationary stop is not encountered, no adverse force correcting any tilting or cocking of the headrest is developed. Indeed, the latch bars may catch teeth of the two catch bars at mutually different elevations above the base floor.

In the just described embodiment the teeth tips 30 are equally spaced. Though this has been found to work well, such is not necessary. Progressive teeth spacing may be had, for example, in conjunction with the use of springs that exhibit non-linear force/displacement characteristics.

It thus is seen that a chiropractic adjustment device is provided which overcomes limitations associated with those of the prior art as proven by excellent clinical results. Though the primary use of the device has been stated as that of practicing Toggle-Recoil on the atlas, it may be used in conjunction with other chiropractic techniques for adjusting vertebrae. For treatment of thoracic, lumbar, pelvic and sacrum vertebrae the device would be enlarged and the headrest would not necessarily by used to support the patient's head. Also, though the device specifically shown is self standing, it may be incorporated into a table, if desired. Thus, it should be understood that the just described embodiment merely illustrates principles of the invention in one preferred form. Many modifications, additions, and deletions other than those expressly suggested may therefore be made thereto without departure from the spirit or scope of the invention as forth in the following claims:

What is claimed is:

1. A chiropractic adjustment device comprising a base, a headrest mounted to said base for movement along a defined path of travel with respect to said base; a plurality of compression springs mounted between said base and said headrest thereby biasing said headrest away from said base; and latch means for releasably catching and holding said headrest under bias provided by said plurality of compression springs in a plurality of positions relative to said base upon the application of diverse forces to said headrest.

2. The chiropractic adjustment device of claim 1 wherein said base has a pair of upright sides that slidably straddle said headrest.

3. The chiropractic adjustment device of claim 1 wherein said latch means comprises a pair of latch bars operatively associated with a pair of spring biased catches that have a series of catch elements.

4. The chiropractic adjustment device of claim 3 said latch bars are mounted to opposite sides of said headrest and wherein said catches are mounted to opposite sides of said base.

5. A chiropractic adjustment device comprising a base, a pair of catches pivotably mounted to opposite sides of said base, a set of springs mounted atop said base; a headrest mounted upon said set of springs; a pair of latch bars mounted to opposite sides of said headrest in engagement with said pair of catches, and wherein each of said catches includes an elongated bar spring biased against one of said latch bars that has a linear series of teeth configured to catch and hold said latch bars at a plurality of headrest positions under bias of said set of springs.

6. The chiropractic adjustment device of claim 5 wherein said base is formed with upright track means along which said headrest is slidably located.

7. The chiropractic adjustment device of claim 5 wherein the teeth of each of said linear series of teeth are equally spaced from one another.

8. The chiropractic adjustment device of claim 5 wherein each of said catches is mounted to said base for pivotal movement about a pivot axis, and wherein said teeth are pitched downwardly generally towards said axis whereby the latch bars may slide downwardly thereover towards the base but may be caught thereby upon reverse movement of the latch bars.

* * * * *